US00PP27738P3

(12) United States Plant Patent
Klemm et al.

(10) Patent No.: US PP27,738 P3
(45) Date of Patent: Feb. 28, 2017

(54) ***SUTERA* PLANT NAMED 'KLESG14831'**

(50) Latin Name: *Sutera grandiflora*
Varietal Denomination: KLESG14831

(71) Applicant: Klemm+Sohn GmbH & Co. KG, Stuttgart (DE)

(72) Inventors: Nils Klemm, Stuttgart (DE); Katinka Wilde, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 14/545,976

(22) Filed: Jul. 13, 2015

(65) Prior Publication Data

US 2017/0020055 P1 Jan. 19, 2017

(51) Int. Cl.
*A01H 5/02* (2006.01)

(52) U.S. Cl.
USPC ..... Plt./485

(58) Field of Classification Search
USPC ..... Plt./485
See application file for complete search history.

*Primary Examiner* — Susan McCormick Ewoldt
(74) *Attorney, Agent, or Firm* — Bethany Reid Roahrig; Barbara Campbell; Cochran Freund & Young, LLC

(57) ABSTRACT

A new *sutera* plant particularly distinguished by having large blue flowers is disclosed.

1 Drawing Sheet

Genus and species: *Sutera grandiflora*.
Variety denomination: 'KLESG14831'.

BACKGROUND OF THE NEW PLANT

The present invention comprises a new and distinct variety of *sutera*, botanically known as *Sutera grandiflora*, and hereinafter referred to by the variety name 'KLESG14831'. 'KLESG14831' originated from a controlled cross between the proprietary female *sutera* variety 'SG-2009-0077' (unpatented) and proprietary male *sutera* variety 'SG-1985-Scopia GVM' (unpatented).

In August of 2010, the two *sutera* parental lines, 'SG-2009-0077' and 'SG-1985-Scopia GVM' were crossed in Nairobi, Kenya, and seeds were obtained. The seeds were sown and plants were grown for evaluation in Stuttgart, Germany. A plant line was selected in May 2011, which had a blue flower color and subsequently named 'KLESG14831'. In May 2011, 'KLESG14831' was first vegetatively propagated by vegetative cuttings in Stuttgart, Germany. 'KLESG14831' was found to reproduce true to type in successive generations of asexual propagation via vegetative cuttings and in-vitro propagation in Stuttgart, Germany.

CROSS REFERENCE TO RELATED APPLICATIONS

Plant Breeder's Rights for 'KLESG14831' were applied for in Canada on Apr. 2, 2015, Application No. 15-8585. 'KLESG14831' has not been made publicly available or sold more than one year prior to the filing date of this application.

SUMMARY

The following are the most outstanding and distinguishing characteristics of this new variety when grown under normal horticultural practices in Stuttgart, Germany.

1. Blue flower color; and
2. Large flowers.

DESCRIPTION OF THE PHOTOGRAPH

This new *sutera* plant is illustrated by the accompanying photograph which shows the flowers and foliage of the plant. The photograph is of a three-month-old plant grown in a controlled greenhouse environment in Stuttgart, Germany in May 2014.

The colors shown are as true as can be reasonably obtained by conventional photographic procedures.

DESCRIPTION OF THE NEW VARIETY

The following detailed descriptions set forth the distinctive characteristics of 'KLESG14831'. The data which define these characteristics were collected from asexual reproductions by in-vitro cultivation carried out in Stuttgart, Germany. Data was collected on 13-week-old plants grown in a controlled greenhouse environment in Stuttgart, Germany in June 2015. Color references are to The R.H.S. Colour Chart of The Royal Horticultural Society of London (R.H.S.), (2005).

Classification:
- *Family*.—Scrophulariaceae.
- *Botanical*.—*Sutera grandiflora*.
- *Common*.—*Sutera*.
- *Designation*.—'KLESG14831'.

Parentage:
- *Female parent*.—Proprietary *sutera* line 'SG-2009-0077' (unpatented).
- *Male parent*.—Proprietary *sutera* line 'SG-1985-Scopia GVM' (unpatented).

Plant:
- *Habit*.—Trailing, flat.
- *Height*.—6.0 cm.
- *Spread*.—30.0 cm.
- *Life cycle*.—Blooms from spring until September.
- *Form*.—Trailing round.

*Time to produce a rooted cutting.*—4 weeks.
*Time to bloom from propagation.*—5 weeks.
*Lastingness of inflorescence on the plant.*—About 7 days.
*Rooting habit and color.*—Fine, fibrous roots; color is white to cream-white.

Stems:
*Number of stems per plant.*—7.
*Length.*—About 20.0 cm.
*Diameter.*—0.4 cm.
*Internode length.*—About 2.0 cm.
*Color.*—RHS 147B.
*Texture.*—Smooth.
*Anthocyanin.*—Absent.

Leaves:
*Arrangement.*—Single, opposite.
*Average number of leaves per branch.*—About 20, and dependent on the age of the plant.
*Leaf type.*—Simple.
*Leaf variegation.*—Absent.
*Shape.*—Ovate, acute angle to the stem.
*Apex.*—Acute.
*Base.*—Cordate.
*Margin.*—Serrate.
*Length.*—2.0 cm.
*Width.*—2.0 cm.
*Color.*—Immature and mature leaves: Upper surface: RHS 146A. Lower surface: RHS 146B.
*Texture* (*both upper and lower surfaces*).—Leathery.
*Venation type.*—Pinnate.
*Venation color.*—Upper surface: RHS 146A. Lower surface: RHS 146B.
*Fragrance.*—Present.
*Petiole.*—Length: 0.4 cm. Diameter: 0.2 cm. Texture: Smooth. Color: RHS 147 B.

Inflorescence:
*Blooming habit.*—Freely flowering.
*Natural flowering season.*—Spring until September.
*Persistent or self-cleaning.*—Flowers are not really self-cleaning but because of the quantity of flowers, old flowers will not be noticeable.
*Peduncle.*—Absent.
*Quantity of inflorescence per stem.*—About 10.
*Type of inflorescence.*—Flowers are often solitary, most often 2 flowers per node are developed.
*Fragrance.*—Present.

Primary pedicel:
*Color.*—RHS 146D.
*Length.*—0.6 cm to 1.0 cm.
*Diameter.*—About 0.1 cm.
*Texture.*—Pubescent.
*Strength.*—Moderate.

Bud:
*Shape.*—Tubular.
*Diameter.*—0.5 cm.
*Length.*—0.4 cm.
*Color* (*at tight bud*).—RHS 145 C to RHS 90 B.

Corolla (flower):
*Type and shape.*—Single-type, nearly round, lower part tube and funnel shaped formed by 5 fused petals, upper part is salver shaped formed by the partly free petal lobes.
*Corolla, horizontal diameter.*—1.9 cm.
*Corolla, total length.*—1.6 cm.
*Color of throat.*—Inner surface: RHS 23A with white border. Outer surface: RHS 15C.
*Funnel.*—Diameter: 0.4 cm. Texture (both inner and outer surfaces): Smooth.

Petal (lobes):
*Apex.*—Rounded tips.
*Base.*—Fused.
*Margin.*—Entire.
*Color.*—Inner surface: RHS 86D. Outer surface: RHS 94C.
*Texture* (*both surfaces*).—Smooth.
*Length.*—Approximately 1.0 cm.
*Width.*—Approximately 1.0 cm.

Calyx:
*Arrangement and appearance.*—Whorl of 5 sepals surrounding the base of the flower tube, sepals are fused at the base.
*Sepals.*—Color (both surfaces): RHS 141C. Length: 1.1 cm. Width: 0.1 cm. Apex: Acute. Base: Fused. Margin: Entire. Texture (both surfaces): Densely pubescent.
*Secondary pedicel.*—Color: RHS 146C. Length: 0.8 cm. Diameter: 0.1 cm. Texture: Pubescent.

Reproductive organs:
*Stamens.*—Quantity: 4. Filament: Color: RHS 155B. Length: 0.5 cm. Diameter: 0.1 cm. Anther color: RHS 23A. Pollen amount: Abundant. Pollen color: RHS 23A.
*Pistil.*—Quantity per flower: 1. Length: 1.1 cm. Stigma color: RHS 145C. Style color: RHS 145D. Style length: 0.8 cm. Ovary color: RHS 145 D.

Fruit and seed set:
*Capsulates/fruit.*—Color: RHS 144A. Size: 0.6 cm in length and 0.4 cm in width. Shape: Ovate.
*Seeds.*—Color: RHS 20A. Size: 0.1 cm. Shape: Round.

Disease and pest/insect resistance: None observed.

COMPARISON WITH PARENTAL LINE AND KNOWN VARIETY

'KLESG14831' is a distinct variety of *sutera* having a blue flower color. 'KLESG14831' is distinguished from its parents as described in Table 1:

TABLE 1

Comparison with Parental Lines

| Trait | Variety 'KLESG14831' | Female parent 'SG-2009-0077' | Male parent 'SG-1985-Scopia GVM' |
|---|---|---|---|
| Branching | Good | Very good | Medium |
| Flower color | Blue | Light lavender | Violet |

'KLESG14831' is most similar to the *sutera* plant named 'KLESG12346' (U.S. Plant Plant Pat. No. 26,433). Differences between the two varieties are described in Table 2:

TABLE 2

Comparison with Similar Variety

| Trait | Variety 'KLESG14831' | Commercial line 'KLESG12346' |
|---|---|---|
| Flower color | Blue | Darker blue |
| Flower size | Very big; larger than 'KLESG12346' | Big; smaller than 'KLESG14831' |
| Summer performance after rain | Flowers open | Flowers closed |

We claim:

1. A new and distinct variety of *sutera* plant named 'KLESG14831' as illustrated and described herein.

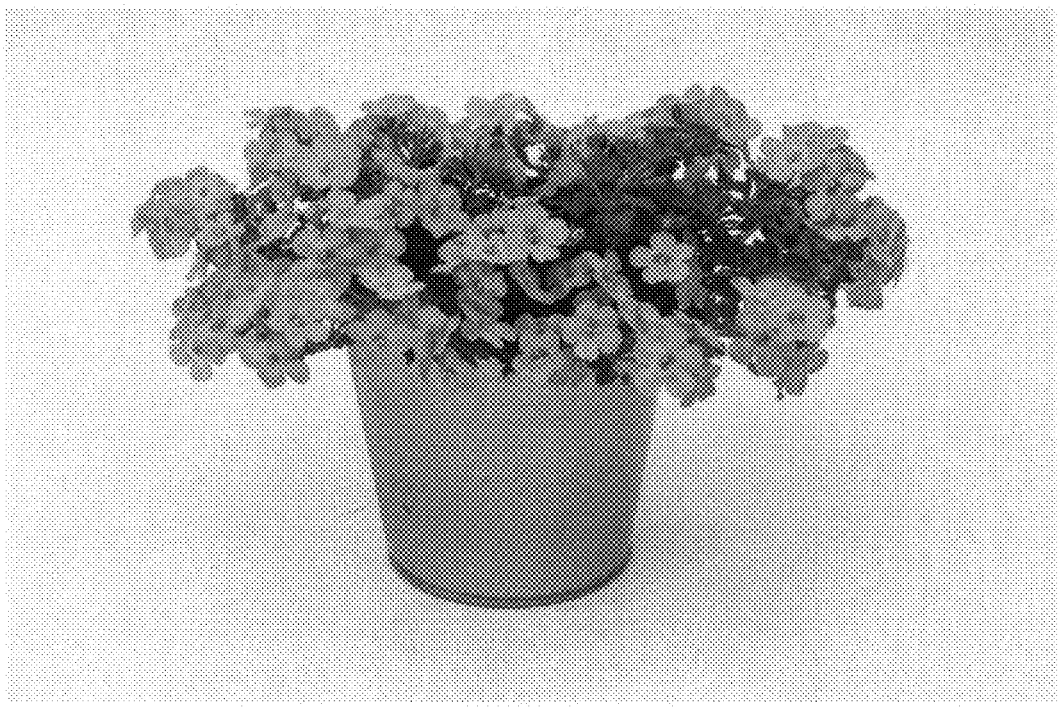

* * * * *